United States Patent [19]

Hane et al.

[11] Patent Number: 4,870,865

[45] Date of Patent: Oct. 3, 1989

[54] DEVICE FOR TESTING FORMATION OF CONNECTION

[75] Inventors: Kazuhiro Hane, Nagoya; Shuzo Hattori, Aichi, both of Japan

[73] Assignee: Nagoya University, Aichi, Japan

[21] Appl. No.: 235,597

[22] Filed: Aug. 24, 1988

[30] Foreign Application Priority Data

Oct. 15, 1987 [JP] Japan .................................. 62-258197

[51] Int. Cl.⁴ ............................................ G01N 21/00
[52] U.S. Cl. ........................................ 73/512; 73/865.3
[58] Field of Search .............. 73/572, 827, 788, 865.3; 250/424, 427

[56] References Cited

U.S. PATENT DOCUMENTS 3,605,486  9/1971  Anderholm et al. .................. 73/788
4,453,414  6/1984  Ronemus et al. ....................... 73/827

OTHER PUBLICATIONS

G. Roussett et al., "Influence of Thermoelastic Bending on Photoacoustic Experiments Related to Measurements of Thermal Diffusivity of Metals", *J. Appl. Phys.*, May 1983.

G. Roussett et al., "A Pulsed Thermoelastic Analysis of Photothermal Surface Displacements in Layered Materials", *J. Appl. Phys.*, May 1985.

Paolo Cielo et al., "Photoacoustic and Photothermal Evaluation of Stratified Materials", *Applied Optics*, Apr. 1986.

*Primary Examiner*—Jerry W. Myracle
*Attorney, Agent, or Firm*—Sughrue, Mion, Zinn, Macpeak & Seas

[57] ABSTRACT

A first laser beam is modulated at a modulation frequency and focused on a first point in the proximity of a connection being tested so as to generate a photothermo elastic wave thereat, and a second laser beam is focused on a second point in the proximity of the connection, which second point is separated from the first point. The second laser beam is scattered at the second point. A detector detects a modulation-frequency component of the scattered second laser beam, so as to detect a propagated level at the second point of the photothermo elastic wave from said first point based on the detected modulation-frequency component of the scattered second laser beam. The propagation of the elastic wave depends on the strength of the connection and the detected level of the elastic wave indicates strength of the connection.

9 Claims, 5 Drawing Sheets

FIG_1

FIG_2

FIG_3

FIG_4

FIG_5

FIG_6

FIG_7

DEVICE FOR TESTING FORMATION OF CONNECTION

BACKGROUND OF THE INVENTION

1. Field of the Invention

This invention relates to a device for testing an electrical connection, and more particularly to a device for testing strength of individual connections in a wiring board, such as a printed wiring board, carrying semiconductor circuit elements mounted thereon.

The invention specifically relates to detection of faulty solder connections, such as those of metallic leads of parts, such as semiconductor circuit elements or packages, to the metal plate of a wiring board.

A test method using the device of the invention is very effective in checking the quality of solder connections in high-density parts, such as packages of semiconductor tips and flat packages of IC (integrated circuit), where inspection by sight and by finger touch is difficult to perform, and image information processing is hardly applicable.

The invention is based on laser-assisted instrumentation and on techniques using the application of photothermo elastic wave generation and the application of optical vibration probing.

2. Description of the Prior Art

Heretofore, no reliable test method has been available to check faulty solder connections in printed wiring boards carrying semiconductor elements. Various methods have been tried, such as a visual inspection method, an image information processing method, and a method using laser beam reflection peculiar to smooth surface of solder wetting, but no reliable and accurate criteria for determination of faulty soldering have been developed yet for practicable inspection of connection formation.

On the other hand, in the field of instrumentation optics using laser beams, a number of research reports have been published in relation to generation of photothermo strain and elastic wave caused thereby: for instance, "measurement of rate of thermal diffusion" by G. Rousset et al, Journal of Applied Physics 54, 2383 (1983); "Non-destructive Inspection of Laminar Material" by G. Rousset et al, Journal of Applied Physics 57, 4396 (1985), P. Cielo et al, Applied Optics 25, 1327 (1986); and "Detection of Defects in Thin plate sample" by K. Hane, T. Kanie, S. Hattori, Applied Optics 27, 386 (1988). However, there have been no reports which concern application of laser beams to detection of faulty soldering or which refer to any possibility of such application.

SUMMARY OF THE INVENTION

Therefore, a general object of the present invention is to provide a novel device for testing electrical connection formation so as to meet the need of reliable detection of the quality of a connection such as soldered connection.

A first object of the invention is to provide a device for detecting a fault in connection formation, the device comprising a means for generating a photothermo elastic wave at a first small point by a focused modulated laser beam and a means for detecting propagation of such elastic wave at a second small point by another laser beam, so that any fault in the connection formation is detected based on variation in the generating and propagating characteristics of the elastic wave due to such fault.

In fact, the device of the invention provides, for the first time in the industry, an automatic technique for checking the quality of connection formation depending on the mechanical strength thereof.

A printed wiring board has very complicated properties for generation and propagation of an elastic wave. However, the inventor has succeeded in providing a practical device for accurately checking the quality of connection formation by properly selecting a point of generation and a point of detection for an elastic wave both in the proximity of the connection formation being tested. The invention is characterized by such use of the elastic wave. As compared with a conventional automatic optical test method, the device of the invention is considerably more effective. One outstanding feature of the invention is that it facilitates an effective test of the quality of connections, even if such connections are in printed wiring boards with high-density packages, or even if such connections are located at the back of the parts or the board and not directly visible from the outside.

In a device according to the invention, a first laser beam emanates from a first laser and becomes incident to a first point in the proximity of a connection to be tested. An example of the connection is a soldered connection between a metallic lead of a part such as an IC package and a printed wiring board, and the first point is on the metallic lead in the proximity of the soldered connection. A modulator, such as a chopper, modulates the first laser beam at a certain modulation frequency. In response to striking by the first laser beam, a photothermo elastic wave is generated at the first point with a repetition rate of the above modulation frequency, and such a wave propagates therefrom.

To detect propagation of the thus generated elastic wave, a second laser directs a second laser beam to a second point in the proximity of the connection. The second point may be located, for instance, on the metallic lead of the part near the first point, but the position of the second point is not restricted to the metallic lead. The second laser beam is scattered at the second point, and an optical detector detects the scattered second laser beam from the second point. The optical detector is connected to the phase-sensitive detector. Thus, the optical detector measures a modulation-frequency component in the scattered second laser beam, and the magnitude of the modulation-frequency component represents intensity of a photo-thermo elastic wave being generated at the first point and propagated to the second point. The strength of the connection is tested based on the thus measured modulation-frequency component of the scattered second laser beam.

A second object of the invention, which relates to a restriction of the scope of the first object, is to further clarify the relationship between the mechanical strength of connection and the generation and propagation properties of elastic wave for the case of more specific formation of the connection, so as to provide a method of selecting proper points of generation and detection of the elastic wave.

(1) In case of a conductor lead having its one end secured to a part or in case of a small circuit element having its one end soldered to a printed wiring board, the intrinsic resonant frequency of such conductor lead or small circuit element varies greatly depending on how rigidly its oppsite end is fixed, such as how strongly its opposite end is fixed by soldering. For instance, when the opposite end is left free, a very strong oscillation of elastic wave may occur. In the above cases, the quality of the connection formation can be checked effectively by selecting both the generation point and the detection point of the elastic wave on the conductor lead or the small circuit element.

(2) When the modulating frequency of a laser beam for generating the elastic wave is high, the attenuation of the elastic wave is large, and the propagation of the elastic wave along a shortest path becomes most salient. When the generation point and the detection point of the elastic wave are selected at opposite sides of a connection formation in close proximity thereto respectively, if the mechanical strength of the connection formation is weak, the elastic wave traveling across the connection formation experiences a large attenuation. Thus, the quality of the connection formation can be easily determined by measuring the strength of the detected elastic wave.

As pointed out above, the selection of the generation point and the detection point of the elastic wave is very important in the device of the invention. In the above-referred two specific cases, faulty connections can be detected and located in a very reliable manner.

A third object of the invention relates to the improvement of the sensitivity in detection of the elastic wave. The amplitude of photo-thermo elastic wave which is generated by a weak laser beam is very small being on the order of 1–1000 pm ($3 \times 10^{-7}$ to $3 \times 10^{-3}$ of light wavelength). To facilitate the detection of such a very small elastic wave, various proposals have been made. The inventor proposes the following methods while considering connection formation of complicated shape such as those in a printed wiring board with a high-density mounting of packages.

(1) When the motion of a body which scatters a laser beam is shown in an amplified manner by variation of a speckle pattern of the thus scattered laser beam, if the amplitude of such variation is represented by X, the rate of variation of light intensity is given by $(\pi X/\lambda)$. When the light-receiving area can be made the same as the area of the speckle pattern, a method for detecting the amplitude of the elastic wave by using the time variation of the speckle image is effective regardless of the conditions of the body being measured, and this method has a high sensitivity.

(2) When the laser beam being detected can be focused within a width $\delta$ at a recessed portion of edge-shape or groove-shape on a body being measured, the scattered laser beam from such recessed portion is concentrated on a plane perpendicular to the edge or groove, and the variation rate of light intensity is given by $X \times \delta$. If the orientation of the edge or the groove is known beforehand, most of the scattered laser beam can be effectively collected. Thus, in such a case, a method of determining the amplitude of elastic wave by using time variation of the edge-type scattered laser beam has a high sensitivity. In the case of measurement on a body which involves an assembly of very small portions, the method using the edge-type scattering is applicable quite frequently.

(3) When a laser beam is divided by a beam splitter and focused on two different points on a scattering body, and then if interference is caused between the scattered laser beams from the two different points, such interference provides an extremely sensitive method for determining the amplitude of the elastic wave, provided that the spacing between the above-referred two different points is selected to be close to the wavelength of the elastic wave and that a difference of the two laser beam paths from the beam splitter to a beam combiner is selected to be one quarter ($\frac{1}{4}$) of the laser beam wavelength. Even when the wavelength of the elastic wave is long, if the elastic wave can be generated locally in a printed wiring board with a high-density mounting of packages, an immovable point can be easily selected and the amplitude of vibration relative to the immovable point can be measured, and the method is quite suitable for the detection of the elastic wave.

As can be understood from the above, one of the characteristics of the invention is that a criterion is provided for selecting the best out of a number of different highly sensitive methods depending on the specific conditions of the body being measured.

A first ancillary object of the invention is to suggest the use of different wavelengths for the first laser beam to generate the elastic wave and for the second laser beam to detect the elastic wave, so that the detector for receiving the scattered second laser beam is prevented from being affected by any scattered portion of the modulated first laser beam by a body other than the body being measured. The intensity variation of the second or detecting laser beam due to the presence of the elastic wave is very small as pointed out above. Thus, influence of scattered light from the first or elastic-wave-generating laser beam on the second laser beam detector is quite disturbing. Under such conditions, it is a very useful to use different wavelengths in the first and second laser beams and to detect the two laser beams of different wavelengths separately by a narrow-band filter.

A second ancillary object of the invention is to suggest a method of determining a criterion of amplitude of the detected elastic wave for determining the quality of connection formation in the device of the invention. The level of amplitude of the elastic wave which is generated in a printed wiring board with a high-density mounting of packages by the device of the invention varies over a wide range, and it is not simple to set a standard level for use in the determination of the quality of connection formation.

The inventor has found it necessary to select two sets of generation points and detection points of the elastic wave for determining the quality of the connection formation, while considering the effects of the quality of the connection formation on the generation and propagating conditions of the elastic wave. The amplitude of the elastic wave should be compared by using the above two sets. In fact, the inventor has suggested scanning the connection formation being checked by moving the generation points and the detecting points of the elastic wave, or by changing the relationship between the generation point and the detection point of the elastic wave. Such scanning is effective not only in obtaining the overall view of the connection formation, but also in determining whether measurements by the above-referred two sets interfere with each other or not by possible accidental change of circumstances between the two sets provided that measurements involving the two sets are not carried out simultaneously.

The device of the invention is very effective in detecting the wetting of solder in the process of soldering to make electric connection. The device of the invention is also effective in checking the quality of connection formation made by other methods, for instance by supersonic welding.

BRIEF DESCRIPTION OF THE DRAWINGS

For a better understanding of the invention, reference is made to the accompanying drawings, in which.

Throughout different views of the drawing, 1 is a first laser, 2 is a chopper, 3 is a part, 4 is a printed wiring board, 5 is a second laser, 6 is an optical detector, 7 is a lock-in amplifier, 8 is a signal generator, 9 is a rough surface, 10 is an observation plane, 11 is an edge-diffraction type scattered laser beam, 12 is a diffraction grating, 13 is a lens, 14 is a beam splitter, 15 is a phase equalizer, 6, 18, 19 are measured value curves for sound solderings, and 17 is a measured value curve for a faulty soldering.

DESCRIPTION OF THE PREFERRED EMBODIMENT

The invention will be described in further detail now by referring to embodiments illustrated in the drawings.

Figure 1:
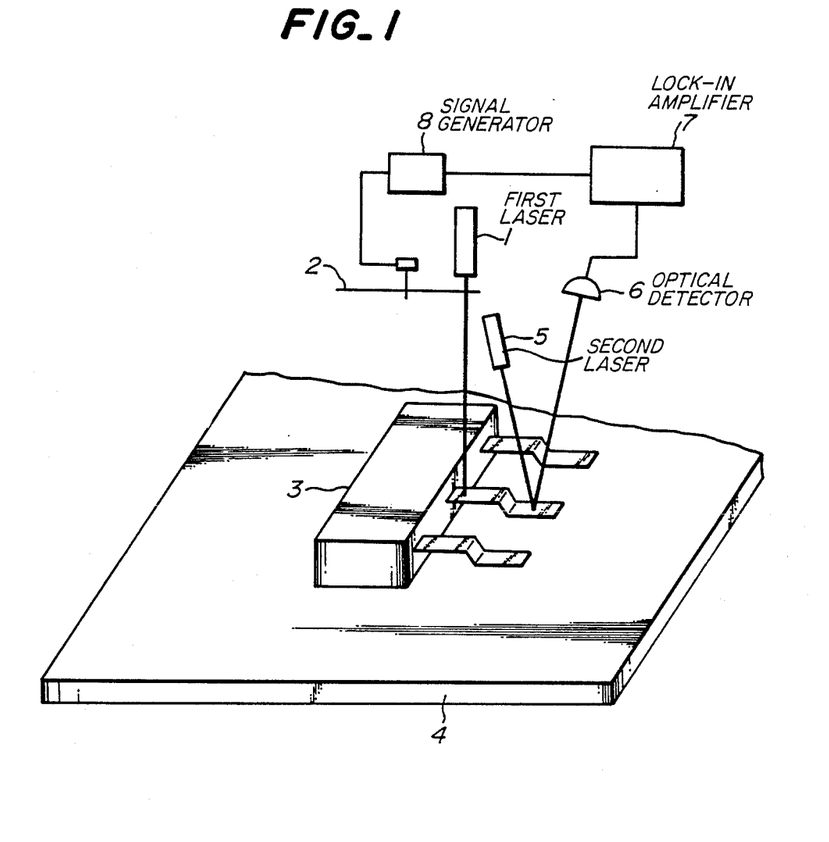
FIG. 1 is a block diagram showing the fundamental structure of a device for checking connection formation according to the invention.

FIG. 1 is a block diagram of the fundamental structure of a device for testing connection formation according to the invention. The first laser beam from a first laser 1 is modulated by a chopper 2, and the modulated laser beam is directed to a first point in the proximity of a connection or joint to be tested. In the illustrated example, the first point is on a part 3 such as an IC package or a circuit element. Most of the energy of the incident first laser beam is absorbed by the part 3 in the form of heat, and thermal elastic strain is generated in phase with the modulation frequency of the chopper 2. The thermal elastic strain wave thus generated propagates as an elastic wave through the electronic part 3 and a printed wiring board 4 to which the part 3 is connected. The propagated elastic wave is detected by a second laser beam from a second laser 5. Moreover particularly, the second laser beam becomes incident to the connection in the proximity of the first point, and reflection of the second laser beam from the second point represents the magnitude of the propagated elastic wave at the second point.

The reflected second laser beam enters an optical detector 6. That portion of the amount of light received by the optical detector 6 which is in phase with the modulation frequency of the chopper 2 is detected by a lock-in amplifier 7 at a high sensitivity. The modulation frequency is generated by a signal generator 8 and simultaneously applied not only to the chopper 2 but also to the lock-in amplifier 7 as a reference signal.

Figure 2:
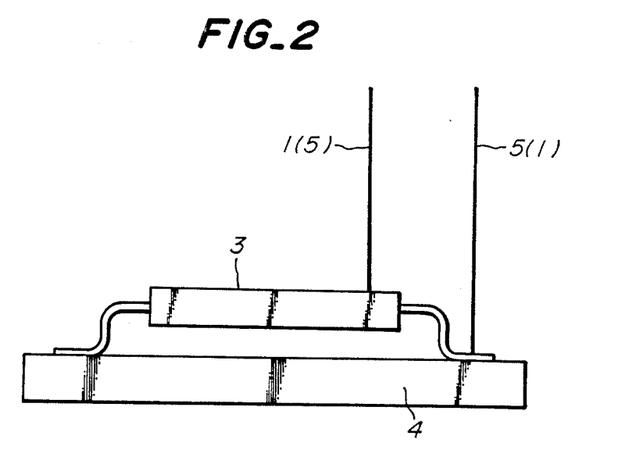
FIG. 2 is an explanatory diagram showing paths of first and second laser beams in the case that the two laser beams are both incident on a metallic lead of a part at first and second points on such metallic lead.

The positional relationship between the two incident points of the first and second laser beams will be described now. There are three different cases of the relationship between the two laser beam incident points; namely, (1) both the first and second points are on the part 3, (2) the two points are on different members, the first point being on the part 3 and the second point being on the printed wiring board 4 or vice versa, and (3) both the first and the second points are on the printed wiring board 4. FIG. 2 shows the two laser beam incident points located on the part 3. In this case, if the connection such as soldering is faulty at a certain point, the supporting rigidity of the connection is low at such faulty point and a large vibration is caused there by the elastic wave due to the thermal elastic strain. Thus, a large output signal is produced for the faulty connection point such as the faulty soldered point.

Figure 3:
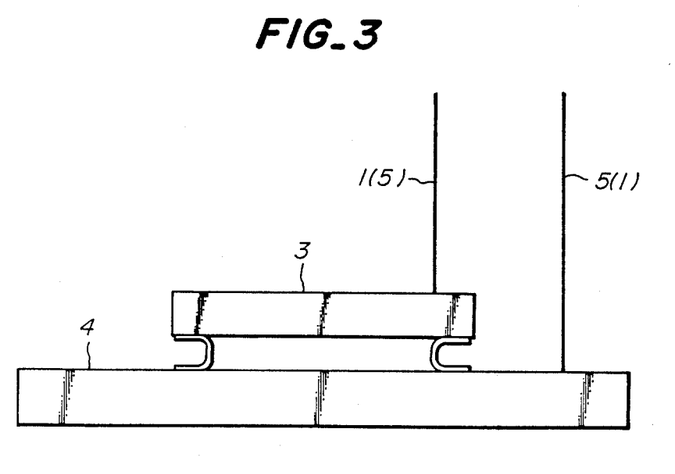
FIG. 3 is an explanatory diagram similar to that of FIG. 2 except that the first and second laser beams are incident on different members, such as an electronic part and a printed wiring board, respectively.

When the two laser beams are directed to opposite sides of a connection, namely when the first laser beam from the first laser 1 is incident on the part 3 while the second laser beam from the secod laser 5 is incident on the printed, wiring board 4 as shown in FIG. 3, the propagation of the photo-thermo elastic wave is disturbed by the presence of a faulty connection. Thus, contrary to the case of FIG. 2, a small output signal is produced for a faulty connection such as a faulty soldered point, as compared with that for a sound connection.

Although the case of the two laser beams which are both directed to the printed wiring board 4 is not illustrated, a faulty connection such as a faulty soldered point in this case can be also detected in a similar manner as described above by referring to FIG. 2.

The optical system for detecting the photothermo elastic wave will be described now. If the second laser beam from the second laser 5 strikes a smooth surface such as a mirror surface, the reflection from such a smooth surface will be also in the form of a laser beam as shown in FIG. 1. When the reflected laser beam is deflected in response to a small displacement of the second point on such a smooth surface due to the propagation of the elastic wave, the beam spot on the optical detector 6 moves, and the photo-thermo elastic wave can be detected as a variation of the amount of light which is received by the optical sensor 6.

Figure 4:
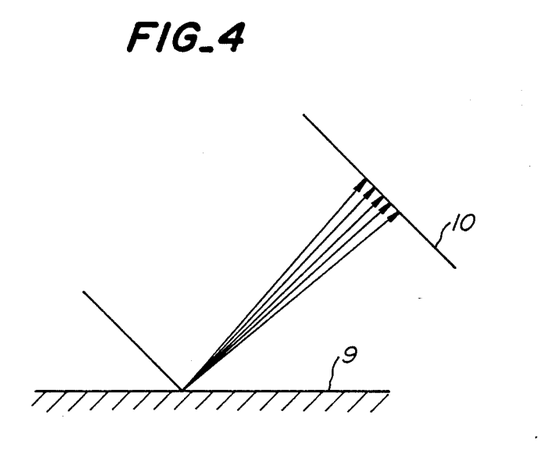
FIG. 4 is an explanatory diagram of the manner in which a speckle pattern of laser beam is generated.
Figure 5:
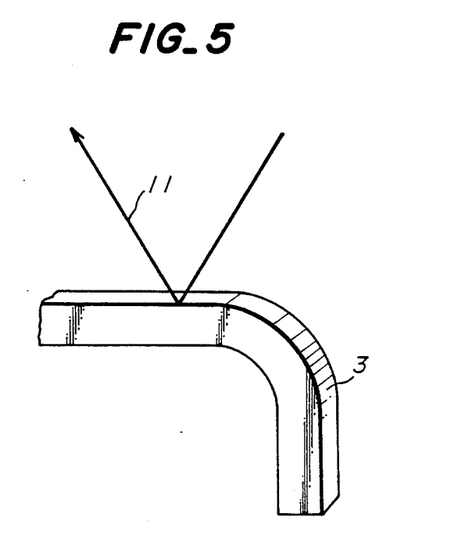
FIG. 5 is an explanatory diagram of edgediffraction type scattering.

In practice, however, the parts 3 and the printed wiring boards 4 usually have rough surfaces. When a laser beam strikes a rough surface 9 as shown in FIG. 4, the laser beam is scattered by the rough surface 9 and the scattered laser beam produces a speckle pattern on an observation plane 10. In response to a small displacement of the rough surface 9 due to the photo-thermo elastic wave, the speckle pattern moves slightly on the observation plane 10. If the optical sensor 6 has a light-receiving port whose area is about the same as the size of a speckle pattern, the photothermo elastic wave can be detected effectively. If an edge of the part 3 is used for causing edge-diffraction in an efficient manner as shown in FIG. 5, measurement comparatively high sensitivity.

Figure 6:
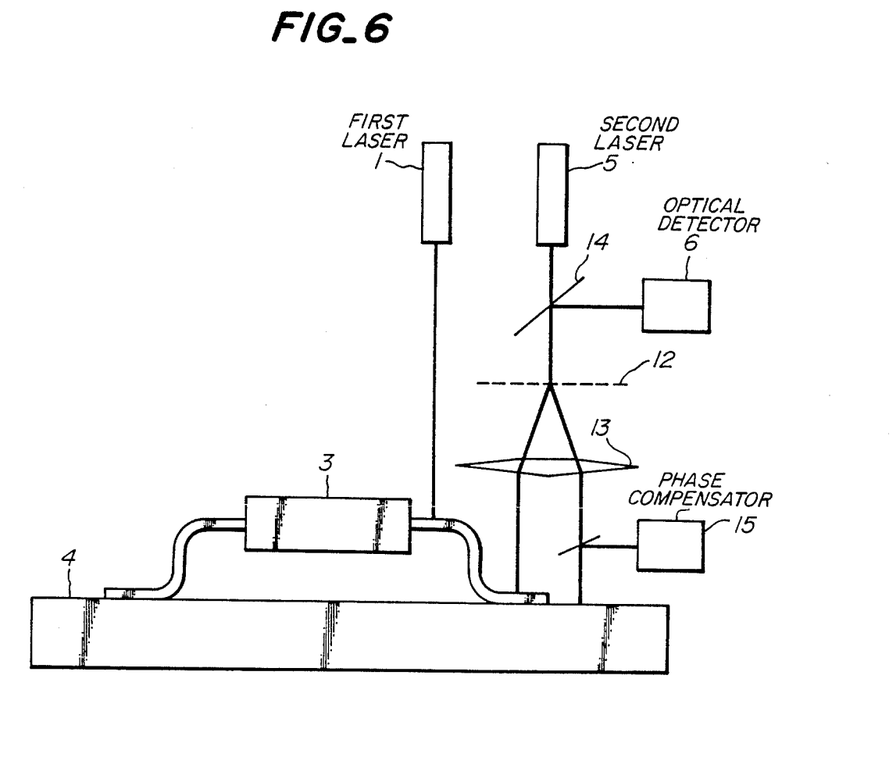
FIG. 6 is a block diagram showing the structure of an interferometer-type device for checking connection formation according to the invention.

FIG. 6 shows a simplified block diagram of an arrangement for detecting the photo-thermo elastic wave by using an interferometer. The first laser 1 directs its first laser beam to the first point on the part 3 so as to generate an elastic wave there. The elastic wave thus generated is detected by a two-laser-beam interferometer. In the illustrated example, the laser beam from the second laser 5 is divided into two laser beams by a diffraction grating 12, and a lens 13 focuses the two laser beams so as to make the incident on the part 3 and the printed wiring board 4, respectively. Reflected laser beams from the part 3 and the board 4 proceed along the same paths as the incident paths, and a beam splitter 14 directs the reflected laser beams to the optical detector 6 so as to measure the intensity of interference. For simplicity, FIG. 6 does not show the modulator, the signal generator and the lock-in amplifier, but they are also used in this example.

The illustrated interferometer uses two separate laser beams with a small spacing therebetween, so that it is hardly affected by vibration from the outside and it can detect the photo-thermo elastic wave with a high sensitivity. The two laser beams are focused by the lens 13 at very fine points respectively, so that even if the reflecting plane is a rough surface, the wave front of the laser beam is hardly disturbed, and a sufficiently high intensity of interference can be achieved. To measure a very small displacement, it is necessary to adjust the phase of the wave front so as to maximize the intensity to be detected. In the illustrated example, a phase compensator 15 formed of a glass plate is inserted in the optical path of one of the two laser beams. Stable detection of the displacement is ensured by maintaining an optimal difference of optical paths through feedback control of the inclination of the glass plate of the phase compensator 15. The use of the interferometer of FIG. 6 facilitates highly sensitive detection of photoelastic wave in a manner similar to that of FIG. 1.

Figure 7:
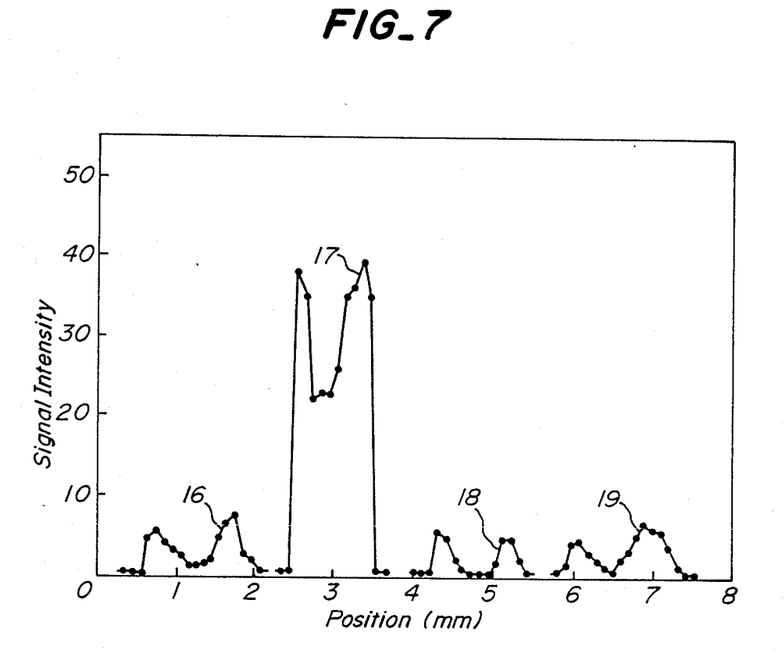
FIG. 7 is a graph showing measured values of signal strength from a device of the invention at different measuring positions for both sound soldering and faulty soldering.

Experiments were carried out by using a combination of the measuring system of FIG. 1 and the speckle pattern detection of FIG. 4. Some examples of measured data of the experiments are shown in FIG. 7. A semiconductor laser for a wavelength of 830 nm was used as the first laeer 1 of the first laser beam, while a He-Ne laser for a wavelength 633 nm was used as the second laser 5 of the second laser beam. Both the first laser beam and the second laser beam were directed onto the part 3 as shown in FIG. 2. More specifically, the first laser beam was incident on to the root portion of a leg of the part 3, while the second laser beam was incident on the tip of the leg of the part 3. The quality of soldered connections of four legs of the part 3 were tested by scanning them with the two laser beams, namely by moving the first and second laser beams relative to the printed wiring board 4. The output from the first laser 1 was about 20 mW, while the output from the second laser 5 was about 1 mW.

The ordinate of the graph of FIG. 7 represents the amplitude or magnitude of the detected signal, while its abscissa represents measured positions in terms of distances from a reference point. Four curves 16, 17, 18 and 19 of the measured values correspond to the four legs of the part 3, respectively. The curve 17 indicates the soldering of the corresponding leg is faulty. The intensity of the signal of the curve 17 is considerably higher than those of the other three curves which represent sound soldering. In this case, the faulty soldering caused a large photo-thermo elastic wave vibration. It was proved that the intensity of the detected signal had a sufficiently large difference depending on the quality of connection being tested so as to detect faulty soldering.

As described in detail in the foregoing, the present invention provides, for the first time in the industry, an automatic testing device for checking the quality of such actual connections as those in printed wiring board with packages mounted theren and the like, based on the mechanical strength thereof. Although a printed wiring board has highly complicated characteristics of generation and propagation of elastic waves, the inventor has succeeded in checking the quality of each connection of such board in a very clear fashion simply by properly selecting generating and detecting points of the elastic wave in the proximity of the connection. The invention is characterized in that it actually provides a device for carrying out such checking of the connection quality, and the device of the invention has an outstanding effects in the ease and accuracy of the measurement as compared with conventional optical automatic checking methods. The invention provides a very peculiar contribution to the industry by enabling effective checking of connections in printed wiring board having a very high density of packages mounted thereon and invisible connections at the back of packages or parts.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. A device for testing formation of electronic connection, comprising a first laser outputting a first laser beam directed to a first point in the proximity of a connection to be tested, a modulator for modulating the first laser beam at a modulation frequency, a second laser outputting a second laser beam directed to a second point in the proximity of the connection, and an optical detector for detecting scattering of the second laser beam from the second point, the optical detector being in phase with the modulating frequency of the modulator so as to measure a modulation-frequency component in the scattered second laser beam, the modulation-frequency component representing intensity of that photo-thermo elastic wave which is generated at the first point and propagated to the second point, whereby strength of the connection is tested based on thus measured modulation-frequency component of the scattered second laser beam.

2. A device for testing formation of connection as set forth in claim 1, wherein said connection is between a circuit element and a printed wiring board, said first point and said second point are both on the circuit element side of the connection, and said modulationfrequency component of the scattered second laser beam increased with decrease of strength of the connection.

3. A device for testing formation of connection as set forth in claim 1, wherein said connection is between a circuit element and a printed circuit board, and said first point and said second point are both on the printed wiring board side of the connection.

4. A device for testing formation of connection as set forth in claim 1, wherein said connection is between a circuit element and a printed circuit board, said first point and said second point are on opposite sides of the connection, and said modulation-frequency component of the scattered second laser beam decreases with decrease of strength of the connection.

5. A device for testing formation of connection as set forth in claim 1, wherein said modulation-frequency component of the scattered second laser beam is measured by detecting time variation of speckle distribution of the scattered second laser beam in phase with the modulating frequency.

6. A device for testing formation of connection as set forth in claim 1, wherein said scattered second laser beam is an edge-diffraction type scattered laser beam, and said modulation-frequency component of the scattered second laser beam is measured by detecting time variation of the edge-diffraction type scattered laser beam in phase with the modulation frequency.

7. A device for testing formation of connection as set forth in claim 1, wherein said device further comprises a diffraction grating disposed in an optical path of said second laser beam so as to divide the second laser beam and focus the divided laser beam on the second point and on a third point in the proximity of the connection, and a interferometer measuring interference between the scattered laser beam from the second point and a scattered laser beam from the third point, whereby said modulation-frequency component is measured by detecting time variation of intensity of interference between scattered laser beam from the second point and the scattered laser beam from the third point in phase with the modulation frequency.

8. A device for testing formation of connection as set forth in claim 1, wherein a frequency of said first laser beam differs from that of said second laser beam, so that said detector detecting the scattered second laser beam is prevented from being affected by the modulation-frequency component of the first laser beam.

9. A device for testing formation of connection as set forth in claim 1, wherein the device further comprises a scanning means for scanning the connection by moving at least one of said first and second points relative to the connection, so as to test the strength of different portions of the connection by measuring modulation-frequency components of the scattered second laser beam at each of the different portions.

* * * * *